US009079035B2

(12) United States Patent
Sanghera et al.

(10) Patent No.: US 9,079,035 B2
(45) Date of Patent: *Jul. 14, 2015

(54) ELECTRODE SPACING IN A SUBCUTANEOUS IMPLANTABLE CARDIAC STIMULUS DEVICE

(71) Applicant: Cameron Health, Inc., San Clemente, CA (US)

(72) Inventors: Rick Sanghera, San Clemente, CA (US); Eric F. King, Santa Ana, CA (US); Don E. Scheck, Carlsbad, CA (US); Abdulkader O. Sudam, Laguna Niguel, CA (US); Jay A. Warren, San Juan Capistrano, CA (US)

(73) Assignee: CAMERON HEALTH, INC., St. Paul, MN (US)

( * ) Notice: Subject to any disclaimer, the term of this patent is extended or adjusted under 35 U.S.C. 154(b) by 58 days.

This patent is subject to a terminal disclaimer.

(21) Appl. No.: 13/911,308

(22) Filed: Jun. 6, 2013

(65) Prior Publication Data

US 2013/0268013 A1    Oct. 10, 2013

Related U.S. Application Data

(63) Continuation of application No. 12/636,569, filed on Dec. 11, 2009, now Pat. No. 8,483,841.

(60) Provisional application No. 61/122,327, filed on Dec. 12, 2008.

(51) Int. Cl.
*A61N 1/04* (2006.01)
*A61N 1/37* (2006.01)
*A61N 1/05* (2006.01)
*A61N 1/39* (2006.01)

(52) U.S. Cl.
CPC .............. *A61N 1/3704* (2013.01); *A61N 1/048* (2013.01); *A61N 1/0504* (2013.01); *A61N 1/0563* (2013.01); *A61N 1/3702* (2013.01); *A61N 1/3968* (2013.01); *A61N 1/3987* (2013.01)

(58) Field of Classification Search
CPC ........ A61N 1/08; A61N 1/0476; A61N 1/048
USPC ........................... 607/5–7, 115; 600/377, 509
See application file for complete search history.

(56) References Cited

U.S. PATENT DOCUMENTS

| | | | |
|---|---|---|---|
| 3,942,536 A | 3/1976 | Mirowski et al. | |
| 4,184,493 A | 1/1980 | Langer et al. | |

(Continued)

FOREIGN PATENT DOCUMENTS

| | | |
|---|---|---|
| EP | 0554208 A2 | 8/1993 |
| EP | 0776674 A1 | 6/1997 |

OTHER PUBLICATIONS

"U.S. Appl. No. 12/625,050, Non Office Action mailed May 23, 2012", 8 pgs.

(Continued)

*Primary Examiner* — Christopher D Koharski
*Assistant Examiner* — Natasha Patel
(74) *Attorney, Agent, or Firm* — Seager, Tufte & Wickhem LLC

(57) ABSTRACT

Methods and implantable cardiac stimulus devices that include leads designed to avoid post-shock afterpotentials. Some examples are directed toward lead-electrode designs that reduce the impact of an applied stimulus on sensing attributes. These examples may find particular use in systems that provide both sensing and therapy delivery from subcutaneous location.

20 Claims, 7 Drawing Sheets

(56) References Cited

U.S. PATENT DOCUMENTS

| | | |
|---|---|---|
| 4,300,567 A | 11/1981 | Kolenik et al. |
| 4,407,288 A | 10/1983 | Langer et al. |
| 4,450,527 A | 5/1984 | Sramek |
| 4,457,315 A | 7/1984 | Bennish |
| 4,567,900 A | 2/1986 | Moore |
| 4,595,009 A | 6/1986 | Leinders |
| 4,603,705 A | 8/1986 | Speicher et al. |
| 4,679,144 A | 7/1987 | Cox et al. |
| 4,693,253 A | 9/1987 | Adams |
| 4,750,494 A | 6/1988 | King |
| 4,779,617 A | 10/1988 | Whigham |
| 4,944,300 A | 7/1990 | Saksena |
| 4,979,110 A | 12/1990 | Albrecht et al. |
| 4,989,602 A | 2/1991 | Sholder et al. |
| 5,000,189 A | 3/1991 | Throne et al. |
| 5,105,810 A | 4/1992 | Collins et al. |
| 5,184,616 A | 2/1993 | Weiss |
| 5,193,535 A | 3/1993 | Bardy et al. |
| 5,203,348 A | 4/1993 | Dahl et al. |
| 5,215,098 A | 6/1993 | Steinhaus et al. |
| 5,217,021 A | 6/1993 | Steinhaus et al. |
| 5,269,319 A | 12/1993 | Schulte et al. |
| 5,271,411 A | 12/1993 | Ripley et al. |
| 5,280,792 A | 1/1994 | Leong et al. |
| 5,292,338 A | 3/1994 | Bardy |
| 5,299,119 A | 3/1994 | Kraf et al. |
| 5,313,953 A | 5/1994 | Yomtov et al. |
| 5,331,966 A | 7/1994 | Bennett et al. |
| 5,342,402 A | 8/1994 | Olson et al. |
| 5,342,407 A | 8/1994 | Dahl et al. |
| 5,342,414 A | 8/1994 | Mehra |
| 5,351,696 A | 10/1994 | Riff et al. |
| 5,366,496 A | 11/1994 | Dahl et al. |
| 5,376,104 A | 12/1994 | Sakai et al. |
| 5,423,326 A | 6/1995 | Wang et al. |
| 5,431,681 A | 7/1995 | Helland |
| 5,447,519 A | 9/1995 | Peterson |
| 5,449,381 A | 9/1995 | Imran |
| 5,476,499 A | 12/1995 | Hirschberg |
| 5,509,924 A | 4/1996 | Paspa et al. |
| 5,522,852 A | 6/1996 | White et al. |
| 5,534,019 A | 7/1996 | Paspa |
| 5,534,022 A | 7/1996 | Hoffmann et al. |
| 5,545,186 A | 8/1996 | Olson et al. |
| 5,558,098 A | 9/1996 | Fain |
| 5,571,163 A | 11/1996 | Helland |
| 5,607,455 A | 3/1997 | Armstrong |
| 5,618,287 A | 4/1997 | Fogarty et al. |
| 5,658,317 A | 8/1997 | Haefner et al. |
| 5,662,697 A | 9/1997 | Li et al. |
| 5,709,215 A | 1/1998 | Perttu et al. |
| 5,755,742 A | 5/1998 | Schuelke et al. |
| 5,776,168 A | 7/1998 | Gunderson |
| 5,817,134 A | 10/1998 | Greenhut |
| 5,827,197 A | 10/1998 | Bocek et al. |
| 5,857,977 A | 1/1999 | Caswell et al. |
| 5,991,657 A | 11/1999 | Kim |
| 5,995,871 A | 11/1999 | Knisley |
| 6,001,095 A | 12/1999 | De La Rama et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Gray |
| 6,148,230 A | 11/2000 | Kenknight |
| 6,157,859 A | 12/2000 | Alt |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,327,498 B1 | 12/2001 | Kroll |
| 6,334,071 B1 | 12/2001 | Lu |
| 6,377,844 B1 | 4/2002 | Graen |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,449,503 B1 | 9/2002 | Hsu |
| 6,493,579 B1 | 12/2002 | Gilkerson et al. |
| 6,493,584 B1 | 12/2002 | Lu |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 | 9/2003 | McClure et al. |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,062,329 B2 | 6/2006 | Ostroff et al. |
| 7,076,289 B2 | 7/2006 | Sarkar et al. |
| 7,085,599 B2 | 8/2006 | Kim et al. |
| 7,117,035 B2 | 10/2006 | Wagner et al. |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner et al. |
| 7,225,035 B2 | 5/2007 | Brabec et al. |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson et al. |
| 7,302,294 B2 | 11/2007 | Kamath et al. |
| 7,330,757 B2 | 2/2008 | Ostroff et al. |
| 7,346,392 B2 | 3/2008 | Kenknight |
| 7,376,458 B2 | 5/2008 | Palreddy et al. |
| 7,379,772 B2 | 5/2008 | Bardy et al. |
| 7,383,091 B1 | 6/2008 | Chitre |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,474,247 B1 | 1/2009 | Heinks |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |

| Patent/Pub No. | Date | Inventor |
|---|---|---|
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,792,585 B1 | 9/2010 | Shelchuk |
| 7,797,036 B2 | 9/2010 | Zhang et al. |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |
| 8,483,841 B2 * | 7/2013 | Sanghera et al. ............ 607/115 |
| 2002/0068958 A1 | 6/2002 | Bardy et al. |
| 2002/0082658 A1 | 6/2002 | Heinrich et al. |
| 2004/0049120 A1 | 3/2004 | Cao et al. |
| 2004/0215239 A1 | 10/2004 | Favet et al. |
| 2004/0215240 A1 | 10/2004 | Lovett et al. |
| 2004/0220628 A1 | 11/2004 | Wagner |
| 2004/0230229 A1 | 11/2004 | Lovett et al. |
| 2004/0254611 A1 | 12/2004 | Palreddy et al. |
| 2005/0107838 A1 | 5/2005 | Lovett et al. |
| 2005/0131464 A1 | 6/2005 | Heinrich et al. |
| 2005/0154421 A1 | 7/2005 | Ousdigian et al. |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | Kenknight |
| 2007/0142736 A1 | 6/2007 | Cazares et al. |
| 2007/0156190 A1 | 7/2007 | Cinbis |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |
| 2007/0232945 A1 | 10/2007 | Kleckner et al. |
| 2007/0232948 A1 | 10/2007 | Stadler et al. |
| 2007/0233198 A1 | 10/2007 | Ghanem et al. |
| 2007/0276445 A1 | 11/2007 | Sanghera et al. |
| 2008/0015647 A1 | 1/2008 | Palreddy et al. |
| 2008/0045850 A1 | 2/2008 | Phillips |
| 2008/0046056 A1 | 2/2008 | O'connor |
| 2008/0077030 A1 | 3/2008 | Ostroff |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |
| 2008/0172098 A1 | 7/2008 | Gunderson et al. |
| 2008/0183085 A1 | 7/2008 | Van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy et al. |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0269835 A1 | 10/2008 | Carlson et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2008/0300497 A1 | 12/2008 | Krause et al. |
| 2009/0036788 A1 | 2/2009 | Nabutovsky et al. |
| 2009/0043352 A1 | 2/2009 | Brooke et al. |
| 2009/0054796 A1 | 2/2009 | Sanghera et al. |
| 2009/0054938 A1 | 2/2009 | Ostroff et al. |
| 2009/0093731 A1 | 4/2009 | Palreddy et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0187227 A1 | 7/2009 | Palreddy et al. |
| 2009/0228057 A1 | 9/2009 | Allavatam et al. |
| 2009/0240157 A1 | 9/2009 | Lian et al. |
| 2009/0240300 A1 | 9/2009 | Lian et al. |
| 2009/0259271 A1 | 10/2009 | Allavatam et al. |
| 2010/0004713 A1 | 1/2010 | Warren et al. |
| 2010/0023084 A1 | 1/2010 | Gunderson |
| 2010/0076515 A1 | 3/2010 | Phillips |
| 2010/0094369 A1 | 4/2010 | Allavatam et al. |
| 2010/0152798 A1 | 6/2010 | Sanghera et al. |
| 2010/0152799 A1 | 6/2010 | Sanghera et al. |
| 2010/0331904 A1 | 12/2010 | Warren et al. |
| 2011/0098585 A1 | 4/2011 | Warren et al. |
| 2011/0098775 A1 | 4/2011 | Allavatam et al. |

OTHER PUBLICATIONS

"U.S. Appl. No. 12/636,569, Non Final Office Action mailed Mar. 15, 2012", 9 pgs.

"U.S. Appl. No. 12/636,569, Non Final Office Action mailed Aug. 20, 2012", 8 pgs.

"U.S. Appl. No. 12/636,569, Notice of Allowance mailed Mar. 4, 2013", 7 pgs.

"U.S. Appl. No. 12/636,569, Preliminary Amendment filed Nov. 5, 2010", 3 pgs.

"U.S. Appl. No. 12/636,569, Response filed Jun. 15, 2012 to Non Final Office Action mailed Mar. 15, 2012", 11 pgs.

"U.S. Appl. No. 12/636,569, Response filed Nov. 19, 2012 to Non Final Office Action mailed Aug. 20, 2012", 11 pgs.

"U.S. Appl. No. 12/636,575, Non Final Office Action mailed Feb. 7, 2013", 8 pgs.

"U.S. Appl. No. 12/636,575, Response filed Mar. 14, 2013 to Non Office Action mailed Feb. 7, 2013", 19 pgs.

"International Application Serial No. PCT/US2009/067781, International Search Report mailed May 4, 2010", 5 pgs.

"International Application Serial No. PCT/US2009/067781, Written Opinion mailed May 4, 2010", 6 pgs.

"International Application Serial No. PCT/US2009/067782, International Search Report mailed May 10, 2010", 3 pgs.

"International Application Serial No. PCT/US2009/067782, Written Opinion mailed May 10, 2010", 6 pgs.

Gunderson, et al., "An Algorithm to Predict Implantable Cardioverter-Defibrillator Lead Failure", JACC, vol. 44, No. 9,, (Nov. 2004), 1898-1902.

Olson, Walter H, et al., "Onset and Stability for Ventricular Tachyarrhythmia Detection in an Implantable Pacer-Cardioverter-Defibrillator", IEEE, (1987), 167-170.

Schuder, John C, "The Role of an Engineering Oriented Medical Research Group in Developing Improved Methods & Devices for Achieving Ventricular Defibrillation: The University of Missouri Experience", PACE, vol. 16, Part I, (Jan. 1993), 95-124.

Schwake, H., et al., "Komplikationen mit Sonden bei 340 Patienten mit einem implantierbaren Kardioverter/Defibrilator", Z Kardiol, vol. 88, No. 8, (1999), 559-565.

Swerdlow, C. D, et al., "Advanced ICD Troubleshooting: Part I", PACE, vol. 26 [Online]. Retrieved from the Internet: <http://www.medscape.com/viewarticle/520588_print>, (Dec. 2005), 1322-1346.

Throne, Robert D, et al., "A Comparison of Four New Time-Domain Techniques for Discriminating Monomorphic Ventricular Tachycardia from Sinus Rhythm Using Ventricular Waveform Morphology", IEEE Transactions on Biomedical Engineering, vol. 38, No. 6, (Jun. 1991), 561-570.

* cited by examiner

ELECTRODE SPACING IN A SUBCUTANEOUS IMPLANTABLE CARDIAC STIMULUS DEVICE

RELATED APPLICATIONS

The present application is a continuation of U.S. application Ser. No. 12/636,569, filed Dec. 11, 2009, now U.S. Pat. No. 8,483,841, which claims the benefit of and priority to U.S. Provisional Patent Application No. 61/122,327, filed Dec. 12, 2008, titled IMPLANTABLE DEFIBRILLATOR SYSTEMS AND METHODS WITH MITIGATIONS FOR SATURATION AVOIDANCE AND ACCOMMODATION, and the disclosure of which is incorporated herein by reference. The present Application is related to U.S. patent application Ser. No. 12/636,575, filed Dec. 11, 2009, published as US Patent Application Publication Number 2010-0152799, now U.S. Pat. No. 8,712,523, titled IMPLANTABLE DEFIBRILLATOR SYSTEMS AND METHODS WITH MITIGATIONS FOR SATURATION AVOIDANCE AND ACCOMMODATION, which also claims the benefit of and priority to U.S. Provisional Patent Application 61/122,327, and is also incorporated herein by reference.

FIELD

The present invention relates to the field of implantable medical devices. More particularly, the present invention relates to subcutaneous implantable cardiac stimulus devices and systems, and leads for use with such devices and systems.

BACKGROUND

Implantable cardioverter-defibrillators (ICDs) are known in the art. Prior devices have included transvenous or epicardial devices. Transvenous devices include leads that reside in blood vessels extending to electrodes placed in the heart. Epicardial devices include electrodes placed on the outside of the heart, usually placed via invasive surgery. New developments in the field include subcutaneous-only systems which lack leads in the vasculature and/or electrodes in or on the heart. Methods and devices configured to respond to new challenges in the subcutaneous ICD space are desired.

SUMMARY

The present invention includes several embodiments that are directed toward lead electrode designs for use in a subcutaneous implantable defibrillator. The following illustrative examples may be embodied in methods of operation, methods of implantation, and/or as implantable components, devices or systems.

DETAILED DESCRIPTION

The following detailed description should be read with reference to the drawings. The drawings, which are not necessarily to scale, depict illustrative embodiments and are not intended to limit the scope of the invention. Any references to other patents or patent applications are intended as illustrative of useful methods or devices and are not intended to foreclose suitable alternatives.

Figure 1:
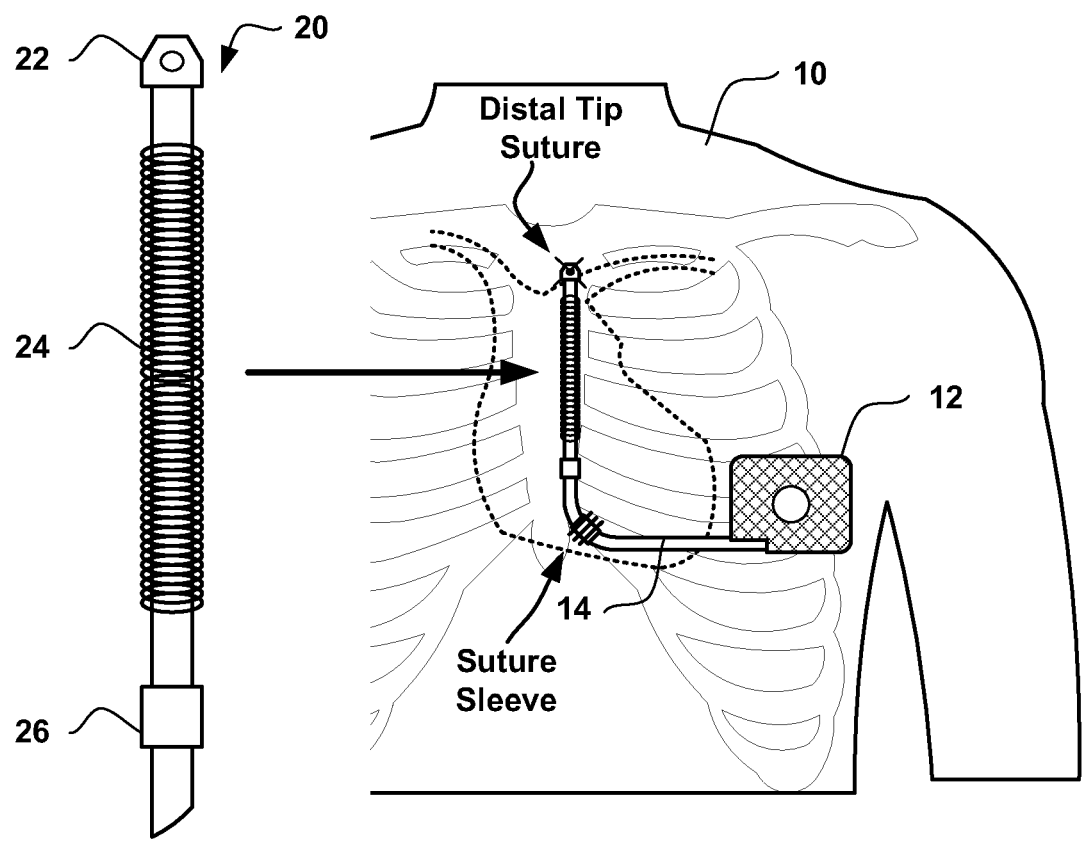
FIG. 1 shows an illustrative subcutaneously implanted system relative to the anatomy of a patient.

FIG. 1 illustrates features of a subcutaneously implanted cardiac stimulus system relative to the anatomy of an implantee 10. The illustrative system includes a canister 12 attached to a lead 14, and both are implanted subcutaneously between the ribcage and the skin of the patient 10. There are no endocardial or epicardial electrodes and no transvenous or intra-thoracic leads in the example shown. The canister 12 is disposed near the left axilla of the patient. The lead 14 extends in a medial direction to approximately the xiphoid and then toward the head of the patient along the left side of the sternum, terminating near the top of the sternum. In an alternative embodiment, one or more leads may be placed in or on the heart in addition to the subcutaneous lead 14, for example, transvenous or epicardial electrodes/leads. The canister 12 may have one or several electrodes, and/or the canister 12 may lack an electrode. Other subcutaneous locations may be used.

As shown in the detail view at 20, the lead 14 includes a distal sensing electrode 22, a therapy delivery coil 24 and a proximal sensing electrode 26. (For the example, "Distal" and "Proximal" refer to position along the lead 14, with the distal electrode 22 being farther from the connection of the lead 14 to the canister 12). The distal sensing electrode 22 may include a suture hole useful for securing the distal sensing electrode 22 to patient tissue during implantation. The canister 12 may also include a suture feature (such as a suture hole in the header) for securing to patient tissue. In some examples, a suture sleeve is used on the lead 14, for example, near the xiphoid, to provide an additional point of fixation or as a substitute for the suture hole on the distal electrode 22. In another example, a suture sleeve may also be placed near the canister 12, either in combination with other fixation points or standing alone. Other fixation structures may be used, without limitation. The lead 14 may include a separate conductor for each electrode 22, 24, 26, and lead 14 may be described as a lead electrode assembly without limiting lead 14 to any particular internal structure or method of manufacture.

Additional illustrative implantation locations and methods of implantation are shown, for example, in commonly assigned U.S. patent application Ser. No. 11/006,291, published as US 2006-0122676 A1 and titled APPARATUS AND METHOD FOR SUBCUTANEOUS ELECTRODE INSERTION, now U.S. Pat. No. 7,655,014, and/or U.S. Pat. Nos. 6,647,292, 6,721,597 and 7,149,575; any of the implantation locations shown in these patents and published applications may be used. Implantation may also be performed by creating incisions at the axilla, xiphoid and termination locations and tunneling therebetween in order to pull the electrode into place using various surgical methods. In one example, an insertion tool is used to tunnel from the xiphoid to the axilla, where an electrode distal end is attached and then pulled back into the xiphoid-axilla tunnel. An insertion tool is then used to tunnel to a termination point superior to the xiphoid along the sternum, with a long suture loop attached at the distal end of the insertion tool and to the electrode distal end. When the tunnel to the termination point is complete, the suture loop is removed from the distal end of the insertion tool, the insertion tool is removed, and the suture loop is used to pull the electrode into the tunnel to the termination point.

In one alternative example, a system is implanted with the canister 12 disposed approximately anterior of the left axilla with the lead 14 extending posteriorly past the axilla to a location over the posterior region of the ribs of the patient, with the distal end of the lead to the left of the spine of the patient, creating an anterior-posterior stimulus vector between the active canister and the coil electrode 24. The '292 patent includes certain unitary embodiments that may also be used, as desired. Other locations may be used and, if desired, a transvenous or epicardial sense or therapy lead may be included.

The system may include any suitable components for detection (such as an input ECG amplifier, filtering circuitry, analog-to-digital conversion circuitry), control (such as memory, a microcontroller and various logic circuits, etc.), telemetry (such as an antenna, amplifier, mixer, transceiver, etc.), power supply (any suitable battery technology may be used) and output circuitry (such as switches, high-power capacitors, and charging circuitry). Any suitable materials may be used for the lead 14 and canister 12. An illustrative example includes a titanium canister 12 having a titanium nitride coating, a polyurethane body for the lead 14 with a silicone sheath thereon, and MP35N conductors in the lead 14 and electrodes 22, 24, 26. Various other materials are known in the art and may be substituted for any of these items. Examples include iridium oxide or porous carbon coatings, platinum or silver electrodes, conductors and/or canister materials, and other materials for the body of lead 14. Drawn filled tubes and/or other structures or materials can be used as conductors in the lead 14.

In order to analyze an implantee's cardiac activity, an implanted medical device captures electrical signals using a combination of at least two implanted electrodes. A detection profile is an analytic tool that can be used to identify cardiac events as perceived from the view of the implantable system. The detection profile is compared to the captured electrical signal(s) and, when the captured signal has a greater magnitude than that represented by the detection profile, a detected event is declared.

Figure 2:
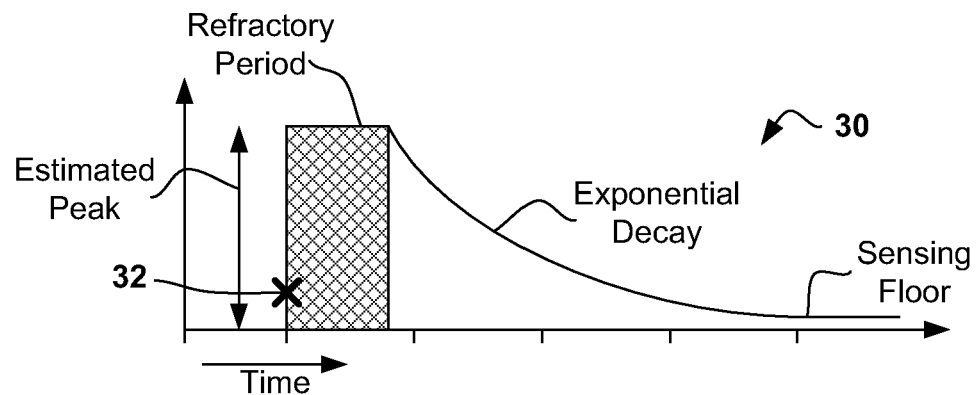
FIGS. 2-3 are graphic representations of detection profiles for use in detecting cardiac events with an illustrative implantable system.
Figure 3:
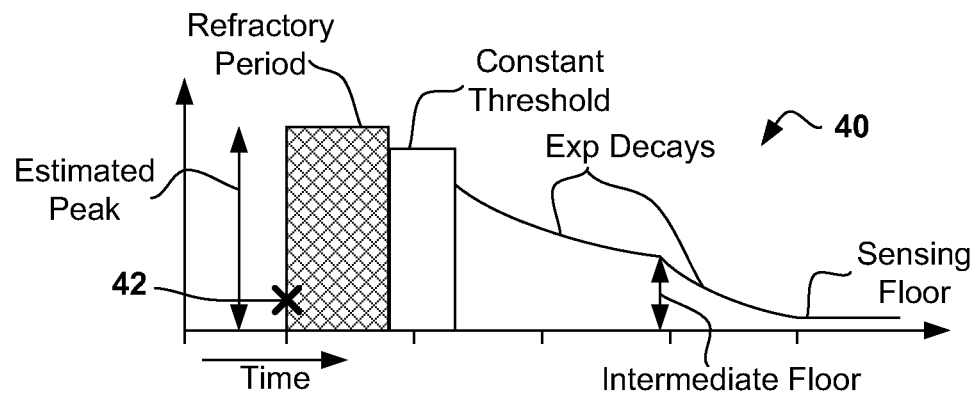

FIGS. 2-3 show illustrative detection profiles. Additional examples and explanations of detection profiles may be found, for example, in U.S. Pat. No. 5,709,215 to Perttu et al. and/or commonly owned U.S. Provisional Patent Application No. 61/034,938, titled ACCURATE CARDIAC EVENT DETECTION IN AN IMPLANTABLE CARDIAC STIMULUS DEVICE, and U.S. patent application Ser. No. 12/399,901, published as US Patent Application Publication Number 2009-0228057, now U.S. Pat. No. 8,565,878, which claims benefit of and has the same title as the 61/034,938 Application. The illustrative detection profiles shown in FIGS. 2-3 vary in amplitude with time. This is typical but not required. The examples in FIGS. 2-3 are for illustrative purposes and it should be noted that the present invention is not contingent/dependent upon any particular form of detection profile, and other methods of cardiac signal analysis may be used instead.

Referring now to FIG. 2, a most recent detected event is represented by the X at 32. Following the most recent detected event 32, the detection profile 30 enters a refractory period during which it does not identify additional cardiac events. The refractory period helps avoid repeatedly sensing the same cardiac event that led to the detected event at 32. A refractory period may last, for example, from tens to hundreds of milliseconds, depending upon the system design.

Following the refractory period, the illustrative detection profile 30 undergoes a decay to a sensing floor. The decay is shown, in FIG. 2 (and FIG. 3) as an exponential decay, although other decay shapes may be used including stepped, straight line, etc. The exponential decay begins at an amplitude proportional to the "estimated peak." The estimated peak is an estimate made by the implanted system of the electrical strength of detected events. For example, an estimated peak may be set to the peak amplitude sensed during the refractory period, a peak from a previous refractory period, or an average of peaks from a plurality of refractory periods. The estimated peak may be replaced with a fixed value. Some examples start exponential decay at 100% of the estimated peak; others use lesser fractions down to as low as 25%. The "sensing floor" is the minimum sensing threshold or, alternatively, defines the maximum sensitivity.

Another detection profile is shown in FIG. 3 at 40. Again, starting with a most recent detected event 42, the detection profile enters a refractory period. The refractory period is followed by a constant threshold period and two exponential decays, first to an intermediate floor and then to the sensing floor. In particular, the detection profile of FIG. 3 provides a number of additional variables that can be manipulated to achieve desired sensing/detection characteristics tailored to individual patients or predetermined conditions. Some examples of these variables include the amplitude of the constant threshold period, the amplitude of the intermediate floor, decay rate(s) associated with the decay periods, and durations for the refractory period, the constant threshold period, and the exponential decays. In one example, durations, thresholds, and decay rates are modified in response to inputs including detected rate, device state, and similarity of estimated peaks for prior detected events. Multiple detection profiles are shown in FIGS. 2-3 in order to indicate that various methods of detection of cardiac events can be suitable.

For each of the examples shown in FIGS. 2-3, it should be appreciated that, for either detection profile 30, 40 a new detected event can be declared as soon as the refractory period ends. If a sufficiently large signal appears at the end of the refractory period, a new event will be declared. This helps to quickly identify fast cardiac rhythms. It also presents the opportunity for saturation of the input circuitry to cause erroneous high-rate calculations. The detection profiles rely in part on stability of the baseline for accurate event detection. Baseline shifts can interfere with accurate sensing of cardiac events by, for example, creating false detections, introducing error into estimated peaks, and/or causing underdetection.

During animal research on a subcutaneous-only system, it was found that a very slow-decaying post-stimulus voltage was present in the region of the coil 24 following delivery of large amplitude stimuli. In some instances, a biphasic defibrillation stimulus was delivered at 80 joules, with a peak (initial) voltage of about 1350 volts, using a 50% tilt (each phase) and 95 microfarad output capacitance.

In one instance, a chronically implanted canine subject received stimulus in response to a high rate tachycardia. Perturbations were observed in the signal captured in the implanted device following stimulus delivery. Analysis suggested correlation of the perturbations to post-stimulus respiratory distress and associated chest movement. In another instance, the effect was replicated in an acutely implanted porcine subject. Transcutaneous manipulation of the lead following stimulus delivery induced perturbations in the detected waveform. In the porcine subject, the post-stimulus perturbations due to manipulation near the sense and coil electrodes on a lead were observable for over an hour after stimulus delivery. Prior to the stimulus delivery, however, no perturbation in the signal could be created by similar transcutaneous manipulation. Various types of physical movement may cause perturbations, such as the patient's voluntary or involuntary movement, external force applied by another person or a machine, and distressed or normal respiration. As a result, frequency selective filtering may be only partly effective. As illustration, FIG. 4 simulates a likely superposition of signals that may have led to these observations.

Figure 4:
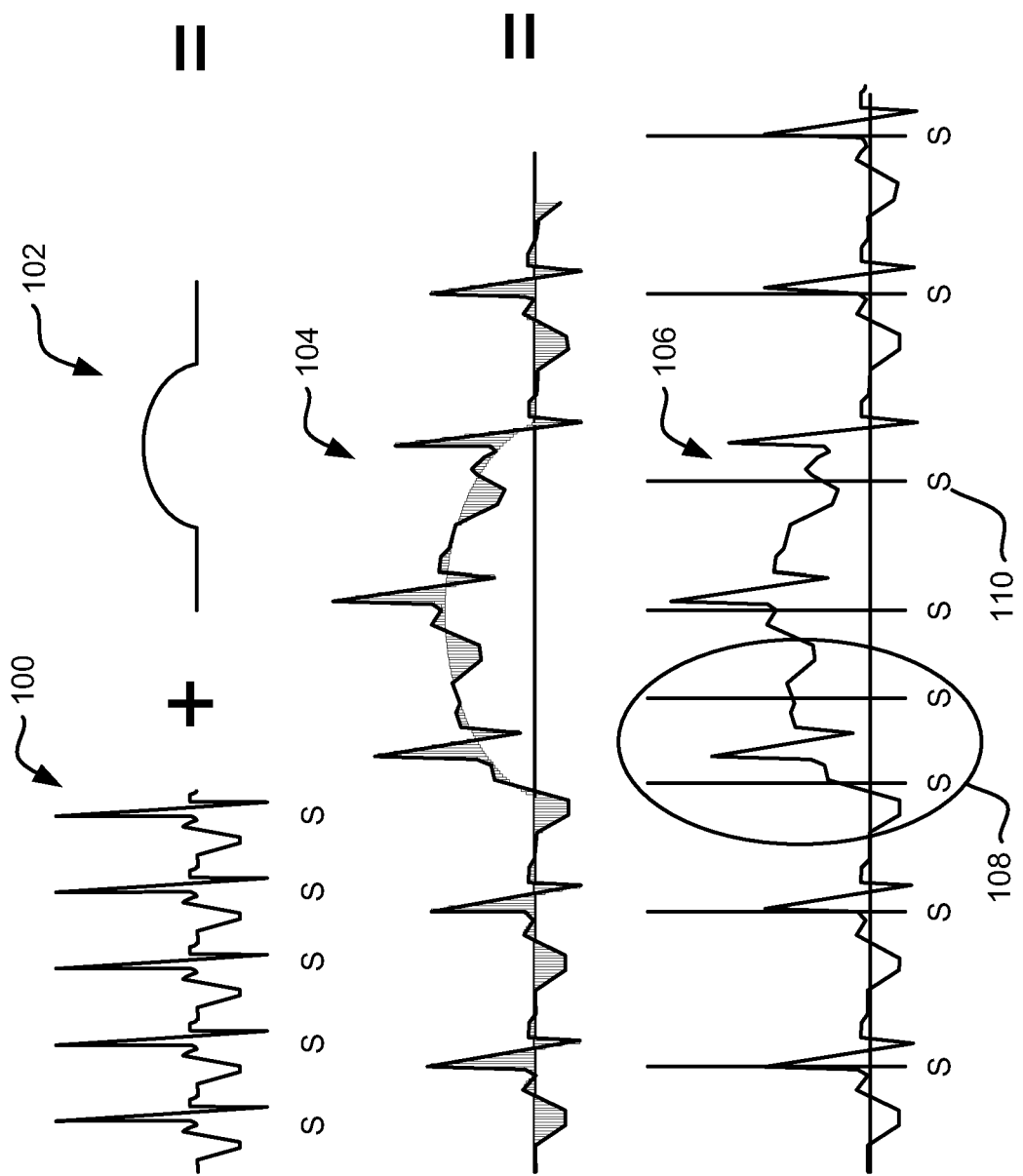
FIGS. 4-5 graphically simulate post-therapy perturbations of ECG signal and potential effects on event detection.

In FIG. 4, the superposition of two signals 100 and 102 is shown. Signal 100 represents a normal cardiac rhythm. The "S" markers indicate beats that would be detected if this signal, by itself, was captured and correctly analyzed by an implantable system. Signal 102 represents a perturbation modeling the kind of perturbation observed due to transcutaneous manipulation of the lead in the porcine model noted above. The observed signal in the canine model was similar. Electrically, the two signals 100, 102 can be combined by superposition to result in a composite signal as shown at 104.

If the composite signal 104 is captured by an implantable device, detection accuracy can be reduced, as shown at 106. In the illustrative analysis at 106, a detection profile as in FIG. 3 was simulated. An extra detection occurs at 108, and the detection at 110 does not align with an R-wave. The detection at 110 could be identified as noise by some systems or, in some systems, morphology analysis may mistake the detection at 110 as a malignant cardiac event.

Figure 5:
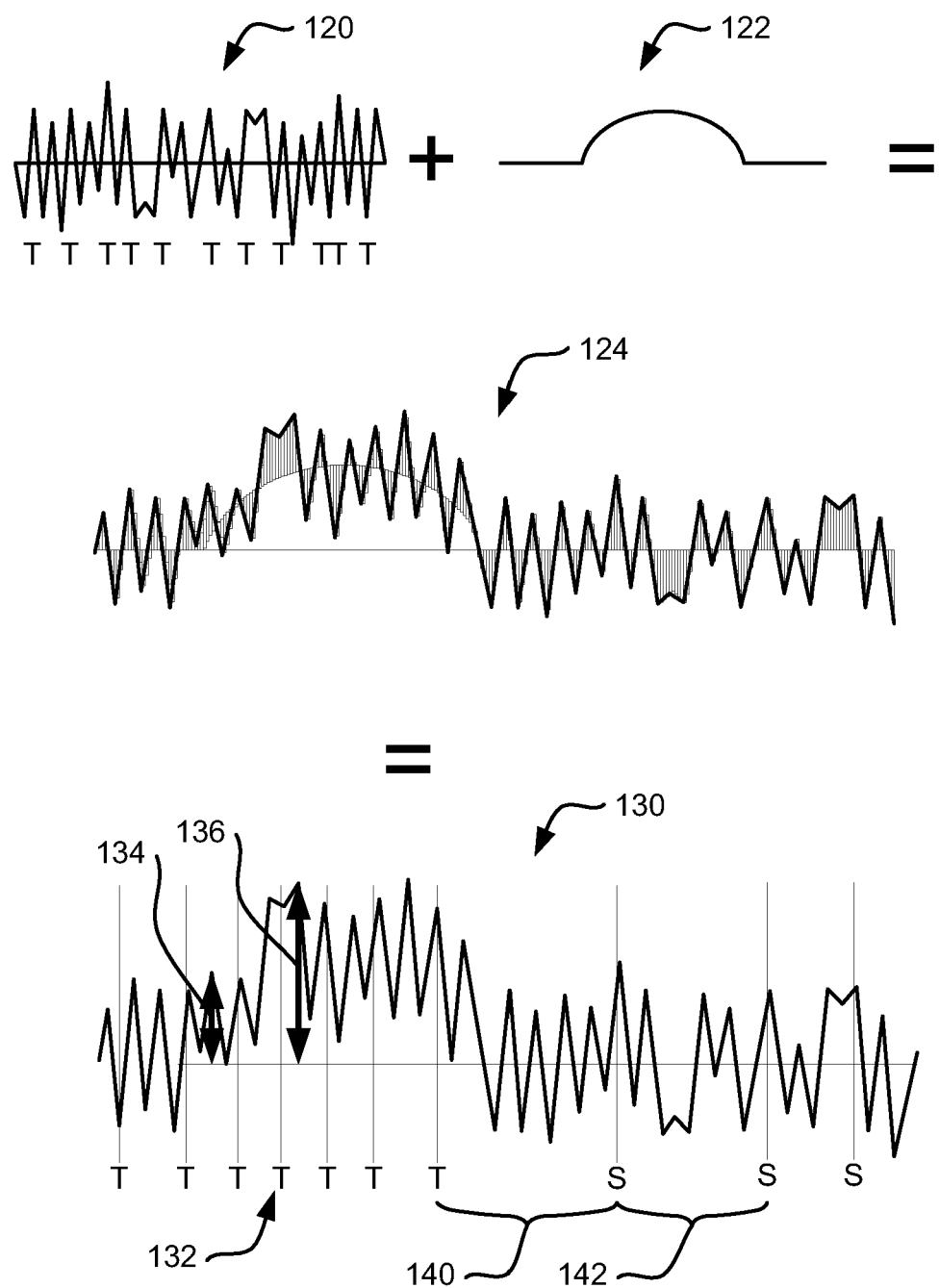

Another simulation is shown in FIG. 5. Here, a lower amplitude tachyarrhythmia is shown and analyzed with more errors than are shown in FIG. 4. A fast rate cardiac signal is shown at 120 (the "T" markers indicate detections identified as indicating tachyarrhythmia). The signal 120 is combined through superposition with a noise perturbation 122, yielding the composite signal 124.

Simulated analysis of the composite signal 124 is shown at 130, using a detection profile as shown in FIG. 3. Large changes in estimated peaks are observed. In particular, the peak amplitude at 134 (due to the cardiac signal alone) is barely half the amplitude at 136 (due to the noise perturbation plus the cardiac signal). In the illustrative example, these peak amplitudes 134, 136 are used to define the height of the subsequent detection profile. One or more large peak amplitudes, such as peak amplitude 136, can raise the detection profile to a level that passes over one or more actual cardiac events.

For example, long detection intervals at 140 and 142 result from undersensing caused by the introduction of large peak amplitudes into the data. Due to the long intervals between detected events, the detection method may begin marking one or more detected events as normal/benign rate (indicated by the "S") rather than tachyarrhythmia (indicated by the "T"). Miscalculation of rate can result from such undersensing.

The potential sensing challenges highlighted in FIGS. 4-5 may not prevent accurate/acceptable operation of a system. For example, filtering and further analysis of the captured signals may be performed to overcome any such difficulties. However, mitigation through modification of the lead could provide an additional tool to improve patient outcomes.

Figure 6:
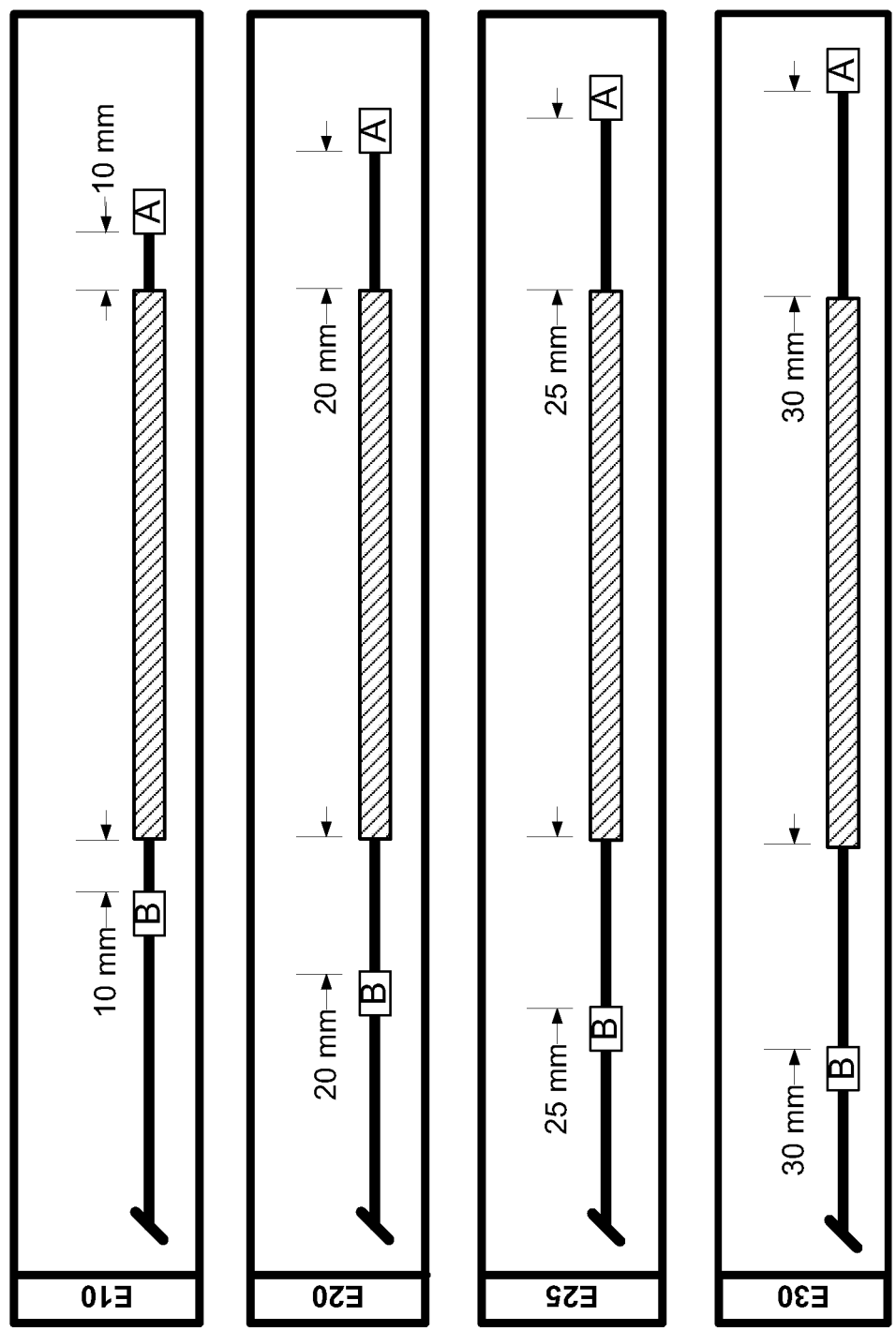
FIG. 6 shows several illustrative lead electrode assemblies.

Some embodiments of the present invention include specific distal electrode structures for a device as shown in FIG. 1. FIG. 6 shows several configurations for a lead electrode assembly labeled E10, E20, E25 and E30. Each configuration includes three electrodes: sense electrodes A and B, with an 80 mm coil electrode disposed therebetween. The labels indicate the approximate distance between sense and coil electrodes for each configuration. The gaps from B to coil and coil to A were as follows:

| {Nominal Values} | B to Coil | Coil to A |
|---|---|---|
| E10 | 10 mm | 10 mm |
| E20 | 20 mm | 20 mm |
| E25 | 25 mm | 25 mm |
| E30 | 30 mm | 30 mm |

The electrode labeled E10 was the subject of the initial investigation of post-shock manipulation in the porcine model described above. It was shown in that investigation that, with transcutaneous manipulation, false detections could be induced following shock delivery with electrode E10. Subsequent investigation compared performance of the four configurations shown in FIG. 6. Configurations E10, E20, E25 and E30 were subjected to testing in which a defibrillation stimulus was applied through the coil electrode and, next, transcutaneous manipulation was performed on the distal portion of the lead electrode assembly to see if false detections could be induced. Further testing was performed in a porcine subject during an acute implantation study. It was decided that overdetections following stimulus (under transcutaneous manipulation) would be used as a measure of the effectiveness of the variation of the spacing proposed in FIG. 6 in reducing the likelihood of post-stimulus overdetection.

The table above provides nominal values. In the tested models the following distances were used:

For E10, B to Coil, 7.3 mm, Coil to A, 8.2 mm, and Coil length 82 mm;

For E20, B to Coil, 19 mm, Coil to A, 19 mm, and Coil length 78 mm;

For E25, B to Coil, 26 mm, Coil to A, 26 mm, and Coil length 82 mm; and

For E30, B to Coil 30 mm; Coil to A, 29 mm, and A to B, 79 mm.

Figure 7:
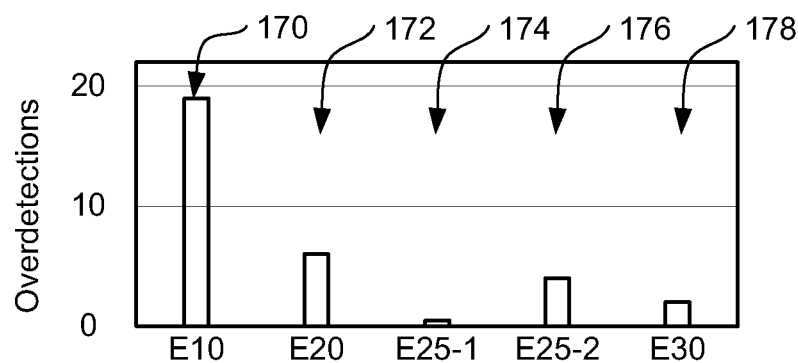
FIG. 7 is a histogram of over-detected events during a test of the lead electrode assemblies of FIG. 6.

FIG. 7 shows the results of testing the configurations E10, E20, E25 and E30. As shown at 170, during a given period of time, nearly 20 overdetections were found during transcutaneous manipulation of the distal lead electrode assembly in the acute porcine study with the E10 electrode. Increasing the interelectrode spacing using the other designs greatly reduced the number of overdetections. As shown at 172, use of E20 reduced the number of overdetections by more than 50%. A first run with E25 produced no overdetections, as shown at 174, so a second run was performed, showing some overdetections, as demonstrated at 176, but less than the number for the E20 electrode. Further reduction was found with the E30 electrode, as shown at 178.

It is believed that the testing performed and analyzed in FIG. 7 shows improved performance as a result of the selected electrode spacing. Interelectrode spacing of 19 mm and more was tested and found to represent an improvement over spacing of less than 10 mm. The improved performance made the system less susceptible to incorrect sensing in the post-shock context. Confirmatory testing was performed and showed that additional electrodes having sense electrode-defibrillation electrode gaps of 19 and 20 mm continued to avoid the perturbations and oversensing following shock delivery with physical manipulation, when compared to that which was observed with the 10 mm nominal gap.

It should be noted that the phenomenon identified in post-stimulus sensing with the subcutaneous-only systems shown above is unlikely to be the same as "stunning" sometimes associated with the effects of high voltage stimulus on myocardial tissue, for example, in transvenous systems. Stunned myocardial tissue typically demonstrates contractile dysfunction and reduced detected amplitude for a temporary period following certain high amplitude stimuli. Because the tissue adjacent the subcutaneous electrodes used in therapy delivery for the systems tested is not myocardial tissue, the observed phenomena is likely of different origin. While systems could operate in the face of this perturbation by using filtering and/or noise detection algorithms, the designs identified herein may enhance post-therapy sensing.

In another illustrative example, one or the other of the sensing electrodes can be omitted. For example, some embodiments make use of a distal tip sensing electrode, but omit the proximal sensing electrode. In other embodiments, the proximal sensing electrode is included, but the distal tip sense electrode is omitted. In yet another example, cardiac signal analysis is performed in the following manner: a default sensing vector is chosen making use of one of three available vectors (referencing FIG. 1): distal sensing electrode 22 to canister 12; proximal sensing electrode 26 to canister 12, or distal sensing electrode 22 to proximal sensing electrode 26, with the default vector selected using, for example, a combination of amplitude and signal-to-noise ratio. Continuing the example, if a vector using the electrode on canister 12 is the default vector, for a period of time after defibrillation is delivered using the canister 12 and coil 24, an alternate vector may be used. In this example, the post-stimulus vector is selected to omit the shock delivery electrodes 12, 24.

Figure 8:
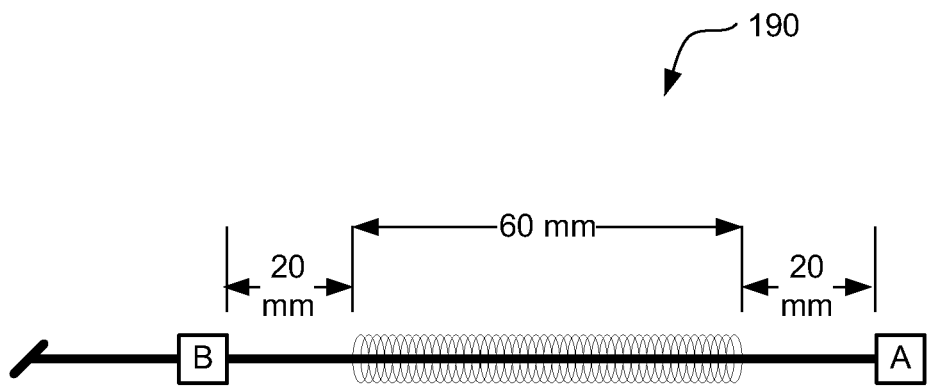
FIG. 8 shows another illustrative lead electrode assembly.

Another design is shown in FIG. 8. A distal portion of a lead electrode assembly is shown at 190. Here, a shorter coil electrode, having a length of about 60 mm, is provided with gaps of nominally 20 mm (actually 19 mm or more) on either side to sense electrodes A and B. The shorter coil electrode may make the implantation location shown in FIG. 1 easier, particularly for patients having a shorter sternum, for example, small adults and/or children. The coil electrode may be shorter still, for example, down to 40 mm or less, if desired.

Figure 9:
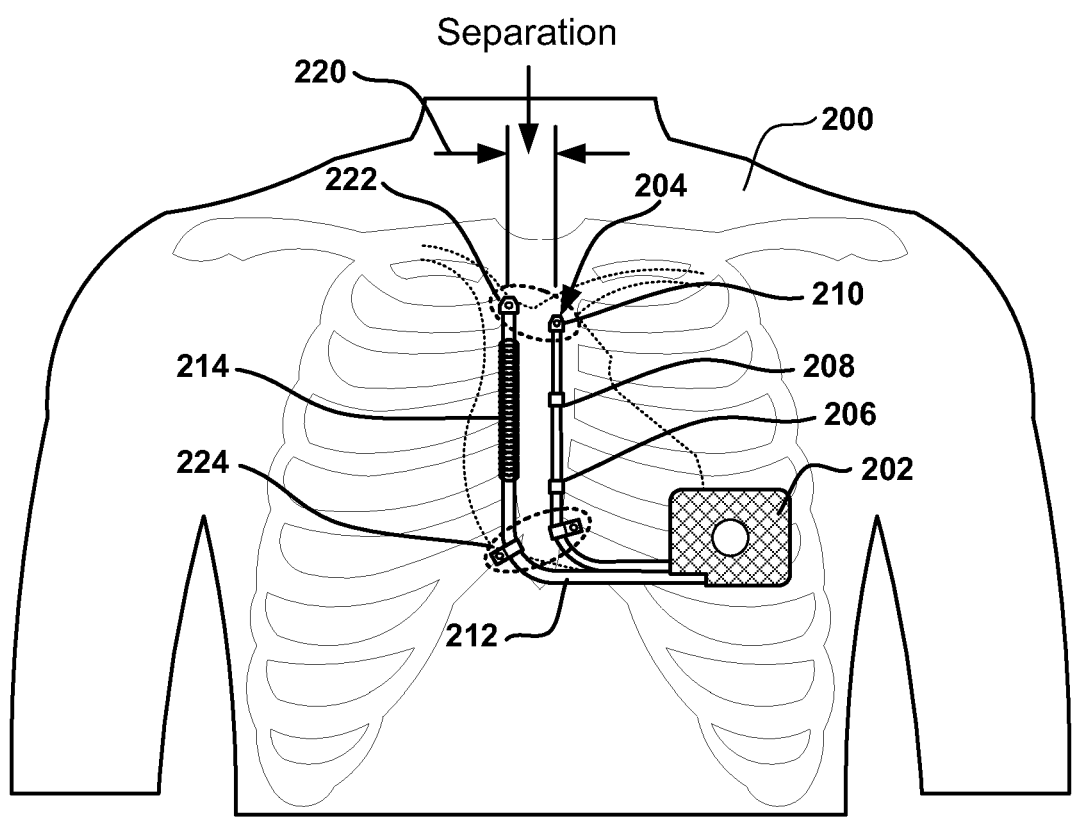
FIG. 9 illustrates an alternative implantation configuration relative to a patient's anatomy.

Another illustrative embodiment is shown in FIG. 9. In this example, an implantee 200 has received an implantable cardioverter defibrillator system that is implanted entirely subcutaneously, generally over the anterior portion of the ribcage. A canister is provided as shown at 202 along the inframammary crease at approximately the left axilla. A sensing lead electrode assembly is shown at 204 as extending vertically along the left side of the patient's sternum and includes several sensing electrodes shown at 206, 208, 210. A stimulus lead electrode assembly is shown at 212 and includes a stimulus coil electrode as shown at 214. The stimulus lead electrode assembly 212 is shown extending to the right of the patient's sternum. In this example, the sensing lead electrode assembly 204 is implanted such that it is spaced by at least a predetermined separation 220 from the stimulus lead electrode assembly 214. The separation 220 may be in the range of about 19 mm or more.

In the example of FIG. 9, each lead electrode assembly may be implanted by dissecting a tunnel. By adequately spacing the tunnels, the lead assemblies 204, 212 may be spaced from one another sufficient to assist sensing operation. Suture sleeve(s) and/or other anchoring features may be used to secure either or both lead assembly 204, 212 with the desired separation 220, as shown at 222, 224. Special implant tools may be used to create this separation 220. For example, an insertion/dissection tool having parallel prongs may be used to establish predicable separation 220.

In another example similar to that of FIG. 9, the separate tunnels on either side of the sternum may be used in the opposite fashion shown, with the shock coil lead 212 being to the left of the sternum and the sensing electrode lead 204 placed on the right of the sternum. This would keep the sensing electrodes outside of the electrical field formed between the shock coil 214 and the canister 202 during defibrillation therapy delivery.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. An implantable defibrillator system for subcutaneous placement comprising:
    an implantable canister housing operational circuitry for sensing electrical cardiac activity and delivering electrical stimulus to correct arrhythmia; and
    a lead electrode assembly comprising:
        a proximal connector end for coupling to the implantable canister;
        a distal end having a distal tip with a distal tip electrode;
        an elongated body extending between the proximal connector end and the distal end; and
        a defibrillation electrode;
    wherein the distal tip electrode is spaced from the defibrillation electrode by a portion of the elongated body having a length of at least nineteen (19) millimeters, with no other electrode therebetween;
    wherein the implantable canister is configured to enable insertion of the lead electrode assembly for operation therewith.

2. The implantable defibrillator system of claim 1 wherein:
    the lead electrode assembly further comprises a proximal sensing electrode proximal of the defibrillation electrode such that the defibrillation electrode is disposed between the proximal sensing electrode and the distal tip electrode; and
    the proximal sensing electrode is spaced from the defibrillation electrode by a portion of the elongated body having a length of at least nineteen (19) millimeters, with no other electrode therebetween.

3. The implantable defibrillator system of claim 2 wherein the spacing between the defibrillation electrode and the distal tip and proximal sensing electrodes is sized such that, following delivery of a defibrillation therapy to a patient, afterpotential is minimized.

4. The implantable defibrillator system of claim 2 wherein the spacing between the defibrillation electrode and the distal tip and proximal sensing electrodes is sized to prevent motion artifact following delivery of defibrillation therapy.

5. The implantable defibrillator system of claim 1 wherein the spacing between the defibrillation electrode and the distal tip electrode is sized such that, following delivery of a defibrillation therapy to a patient, afterpotential is minimized.

6. The implantable defibrillator system of claim 1 wherein the spacing between the defibrillation electrode and the distal tip electrode is sized to prevent motion artifact following delivery of defibrillation therapy.

7. The implantable defibrillator system of claim 1 wherein the spacing between the defibrillation electrode and the distal tip electrode is sized such that, following delivery of an 80 Joule defibrillation therapy to a patient, afterpotential is minimized.

8. The implantable defibrillator system of claim 1 wherein the spacing between the defibrillation electrode and the distal tip electrode is sized to prevent motion artifact following delivery of an 80 Joule defibrillation therapy.

9. The implantable defibrillator system of claim 1 wherein the spacing between the defibrillation electrode and the distal tip electrode is sized such that, following delivery of a defibrillation therapy having a peak voltage of about 1350 volts to a patient, afterpotential is minimized.

10. The implantable defibrillator system of claim 1 wherein the spacing between the defibrillation electrode and the distal tip electrode is sized to prevent motion artifact following delivery of a defibrillation therapy having a peak voltage of about 1350 volts to a patient.

11. An implantable defibrillator system for subcutaneous placement comprising:
    an implantable canister housing operational circuitry for sensing electrical cardiac activity and delivering electrical stimulus to correct arrhythmia; and
    a lead electrode assembly comprising:
        a proximal connector end for coupling to the implantable canister;
        a distal end having a distal tip;
        an elongated body extending between the proximal connector end and the distal end;
        a defibrillation electrode; and
        a proximal sensing electrode proximal of the defibrillation electrode;
    wherein the proximal sensing electrode is spaced from the defibrillation electrode by a portion of the elongated body having a length of nineteen (19) millimeters up to twenty-nine (29) millimeters, with no other electrode therebetween;
    wherein the implantable canister is configured to enable insertion of the lead electrode assembly for operation therewith.

12. The implantable defibrillator system of claim 11 wherein:
    the lead electrode assembly further comprises a distal tip electrode at the distal end such that the defibrillation electrode is disposed between the proximal sensing electrode and the distal tip electrode; and
    the distal tip electrode is spaced from the defibrillation electrode by a portion of the elongated body having a length of nineteen (19) millimeters up to twenty-nine (29) millimeters, with no other electrode therebetween.

13. The implantable defibrillator system of claim 12 wherein the spacing between the defibrillation electrode and the distal tip and proximal sensing electrodes is sized such that, following delivery of a defibrillation therapy to a patient, afterpotential is minimized.

14. The implantable defibrillator system of claim 12 wherein the spacing between the defibrillation electrode and the distal tip and proximal sensing electrodes is sized to prevent motion artifact following delivery of defibrillation therapy.

15. The implantable defibrillator system of claim 11 wherein the spacing between the defibrillation electrode and the proximal sensing electrode is sized such that, following delivery of a defibrillation therapy to a patient, afterpotential is minimized.

16. The implantable defibrillator system of claim 11 wherein the spacing between the defibrillation electrode and the proximal sensing electrode is sized to prevent motion artifact following delivery of defibrillation therapy.

17. The implantable defibrillator system of claim 11 wherein the spacing between the defibrillation electrode and the proximal sensing electrode is sized such that, following delivery of an 80 Joule defibrillation therapy to a patient, afterpotential is minimized.

18. The implantable defibrillator system of claim 11 wherein the spacing between the defibrillation electrode and the proximal sensing electrode is sized to prevent motion artifact following delivery of an 80 Joule defibrillation therapy.

19. The implantable defibrillator system of claim 11 wherein the spacing between the defibrillation electrode and the distal tip electrode is sized such that, following delivery of a defibrillation therapy having a peak voltage of about 1350 volts to a patient, afterpotential is minimized.

20. The implantable defibrillator system of claim 11 wherein the spacing between the defibrillation electrode and the proximal sensing electrode is sized to prevent motion artifact following delivery of a defibrillation therapy having a peak voltage of about 1350 volts to a patient.

* * * * *